(12) United States Patent
Diolaiti

(10) Patent No.: US 9,108,318 B2
(45) Date of Patent: Aug. 18, 2015

(54) SWITCHING CONTROL OF AN INSTRUMENT TO AN INPUT DEVICE UPON THE INSTRUMENT ENTERING A DISPLAY AREA VIEWABLE BY AN OPERATOR OF THE INPUT DEVICE

(71) Applicant: Intuitive Surgical Operations, Inc., Sunnyvale, CA (US)

(72) Inventor: Nicola Diolaiti, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 175 days.

(21) Appl. No.: 13/764,556

(22) Filed: Feb. 11, 2013

(65) Prior Publication Data

US 2013/0211588 A1 Aug. 15, 2013

Related U.S. Application Data

(60) Provisional application No. 61/599,208, filed on Feb. 15, 2012.

(51) Int. Cl.
*B25J 13/06* (2006.01)
*A61B 19/00* (2006.01)
*B25J 9/16* (2006.01)

(52) U.S. Cl.
CPC ............. *B25J 13/06* (2013.01); *A61B 19/2203* (2013.01); *B25J 9/1689* (2013.01); *A61B 19/5212* (2013.01); *A61B 2019/2223* (2013.01); *A61B 2019/5259* (2013.01)

(58) Field of Classification Search
CPC ...... A61B 19/2203; B25J 13/06; B25J 13/08; B25J 13/089; B25J 19/02; B25J 19/021; B25J 19/023; B25J 19/025; B25J 19/04; B25J 9/0084; B25J 9/1643; B25J 9/1664; B25J 9/1666; B25J 9/1669; B25J 9/1676; B25J 9/1682; B25J 9/1689; B25J 9/1697; G05B 2219/40114; G05B 2219/40543
USPC .................................. 700/248–250, 258, 259
See application file for complete search history.

(56) References Cited

U.S. PATENT DOCUMENTS

| 6,102,850 | A | 8/2000 | Wang et al. | |
|---|---|---|---|---|
| 6,645,196 | B1 | 11/2003 | Nixon et al. | |
| 6,659,939 | B2* | 12/2003 | Moll et al. | 600/102 |
| 6,671,581 | B2* | 12/2003 | Niemeyer et al. | 700/245 |
| 6,720,988 | B1* | 4/2004 | Gere et al. | 348/45 |

(Continued)

FOREIGN PATENT DOCUMENTS

KR 20110081153 A 7/2011

OTHER PUBLICATIONS

International Search Report and Written Opinion for Application No. PCT/US2013/025630, mailed on Jun. 2, 2013, 12 pages.

(Continued)

*Primary Examiner* — Jerrah Edwards

(57) ABSTRACT

An operator telerobotically controls instruments to perform a procedure on an object at a work site while viewing real-time images of the work site on a display screen. An assistant controls movement of another instrument towards or away from the work site to relieve the operator from such task. Control of the instrument is automatically switched from the assistant to the operator upon the working end of the instrument entering the view on the display screen.

29 Claims, 14 Drawing Sheets

(56) References Cited

U.S. PATENT DOCUMENTS

| | | | |
|---|---|---|---|
| 7,543,588 B2 | 6/2009 | Wang et al. | |
| 7,725,214 B2* | 5/2010 | Diolaiti | 700/247 |
| 7,865,266 B2 | 1/2011 | Moll et al. | |
| 8,073,528 B2* | 12/2011 | Zhao et al. | 600/424 |
| 8,108,072 B2* | 1/2012 | Zhao et al. | 700/250 |
| 2007/0293721 A1 | 12/2007 | Gilboa | |
| 2008/0004603 A1* | 1/2008 | Larkin et al. | 606/1 |
| 2008/0065108 A1* | 3/2008 | Diolaiti | 606/130 |
| 2009/0326552 A1* | 12/2009 | Diolaiti | 606/130 |
| 2010/0228264 A1 | 9/2010 | Robinson et al. | |
| 2011/0040305 A1 | 2/2011 | Gomez et al. | |
| 2011/0082365 A1* | 4/2011 | McGrogan et al. | 600/424 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SWITCHING CONTROL OF AN INSTRUMENT TO AN INPUT DEVICE UPON THE INSTRUMENT ENTERING A DISPLAY AREA VIEWABLE BY AN OPERATOR OF THE INPUT DEVICE

CROSS REFERENCE TO RELATED APPLICATIONS

This application claims priority to U.S. Provisional Application No. 61/599,208 (filed Feb. 15, 2012), which is incorporated herein by reference.

FIELD OF THE INVENTION

The present invention generally relates to robotic systems and in particular, to a method for switching control of an instrument to an input device upon the instrument entering a display area viewable by an operator of the input device.

BACKGROUND OF THE INVENTION

In a robotic system, a plurality of instruments may be telerobotically controlled by an operator to perform a procedure on an object at a work site. A camera is provided at the work site to capture images of end effectors of the instruments as they interact with the object to perform the procedure, so that the operator may view their movements on a display screen while controlling them through associated input devices.

While performing the procedure, it may be necessary to introduce a new instrument to the work site to perform a needed function; replace an instrument already there with a new instrument; replace an end effector on an instrument already there with a new end effector; introduce some accessory item to the work site for performing the procedure by attaching it to an instrument and inserting the instrument to the work site; or remove an item from the work site by attaching it to an instrument, retracting the instrument and removing the item from the instrument, and reinserting the instrument back to the work site so that it may once again be available for use there.

In each of these applications, it may be advantageous to have an assistant control all or a part of these actions while the primary operator continues to perform the procedure using the remaining instruments. Once the new or the retracted and reinserted instrument becomes available at the work site, its control may be transferred to the primary operator so that the instrument is available for use by the primary operator at the work site.

To insert the new or the retracted and reinserted instrument to the work site, however, may be a time consuming and difficult task for the assistant. Also, it may be difficult for the assistant to bring the new or reinserted instrument into the field of view of the on-site camera so that it may be viewed by the primary operator on the display screen before switching control of the instrument to the primary operator. It is also possible for the assistant to misjudge the depth of insertion of the new or reinserted instrument and place its distal end too deep into the work site, which may cause unintended contact between the instrument and objects at the work site. To avoid such unintended and possibly harmful contact, the assistant is likely to move the new or reinserted instrument very slowly into the work site.

U.S. Pat. No. 6,645,196, which is incorporated herein by reference, describes a guided tool exchange procedure employable in a medical robotic system to guide a new tool quickly and precisely, after a tool exchange operation, into close proximity to the operating position of the original tool prior to its removal from a work site.

During the performance of a procedure, however, the camera pose may change so that the camera may get a better view of the working ends of instruments as the instruments move while performing a procedure on an object at the work site. In such a situation, inserting a replacement or reinserting the old instrument to its former position may be undesirable since it may not be a good location for the new instrument and further because it may be outside the current field of view of the camera. In addition, it may be desirable to allow the primary operator to assume control of the new instrument as soon as practical so as not to unduly delay the continued performance of the procedure using the new instrument.

OBJECTS AND SUMMARY OF THE INVENTION

Accordingly, one object of one or more aspects of the present invention is a robotic system and method implemented therein that switches control of an instrument to an input device upon the instrument entering a display area viewable by an operator of the input device.

Another object of one or more aspects of the present invention is a robotic system and method implemented therein that is compatible with an instrument or tool exchange procedure.

Another object of one or more aspects of the present invention is a robotic system and method implemented therein that prevents harm to an object at a work site while an instrument is being guided to the work site.

Another object of one or more aspects of the present invention is a robotic system and method implemented therein that warns an operator of the robotic system if an insertion of an instrument towards a work site reaches a maximum insertion distance without the instrument entering a display area viewable by the operator on a display screen.

These and additional objects are accomplished by the various aspects of the present invention, wherein briefly stated, one aspect is a robotic system comprising: a camera; an instrument; an input device; and a processor configured to switch control of the instrument to the input device upon determining that the instrument has entered an area of a field of view of the camera.

Another aspect is a method implemented in a robotic system to switch control of an instrument to an input device, the method comprising: switching control of the instrument to the input device upon determining that the instrument has entered an area of a field of view of a camera.

Additional objects, features and advantages of the various aspects of the present invention will become apparent from the following description of its preferred embodiment, which description should be taken in conjunction with the accompanying drawings.

DETAILED DESCRIPTION

Figure 1:
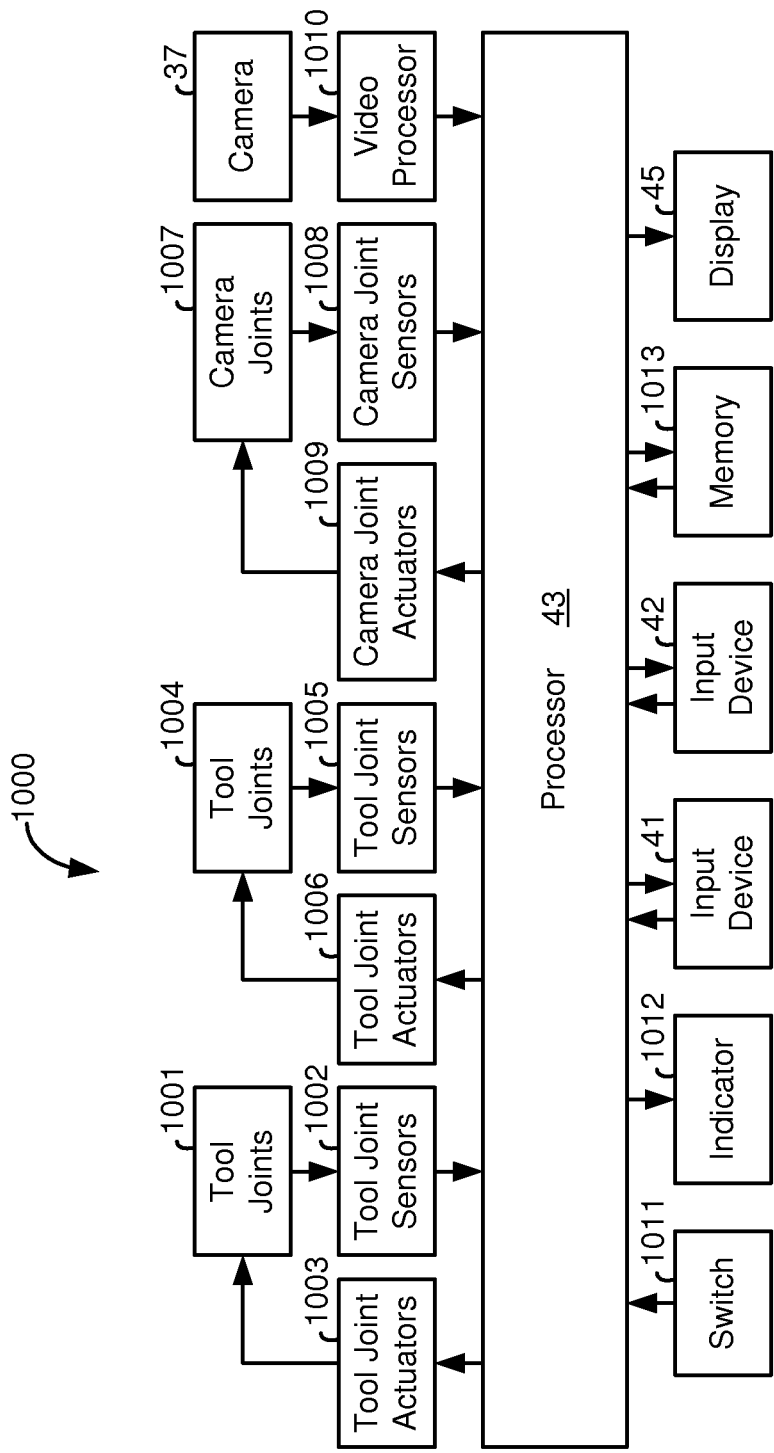
FIG. 1 illustrates a block diagram of a robotic system utilizing aspects of the present invention.
Figure 8A:
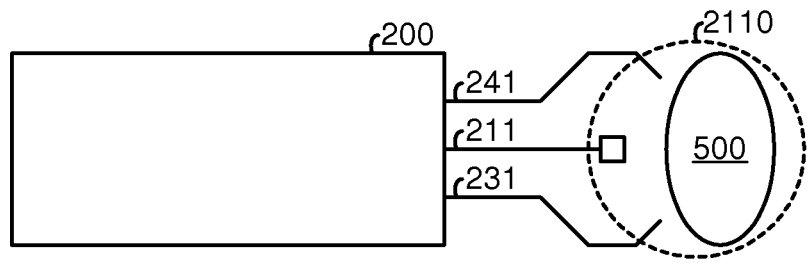
FIGS. 8a-8c illustrate schematic views of articulated instruments at a work site in different stages of a guided tool exchange procedure performed in a single aperture medical robotic system utilizing aspects of the present invention.
Figure 9:
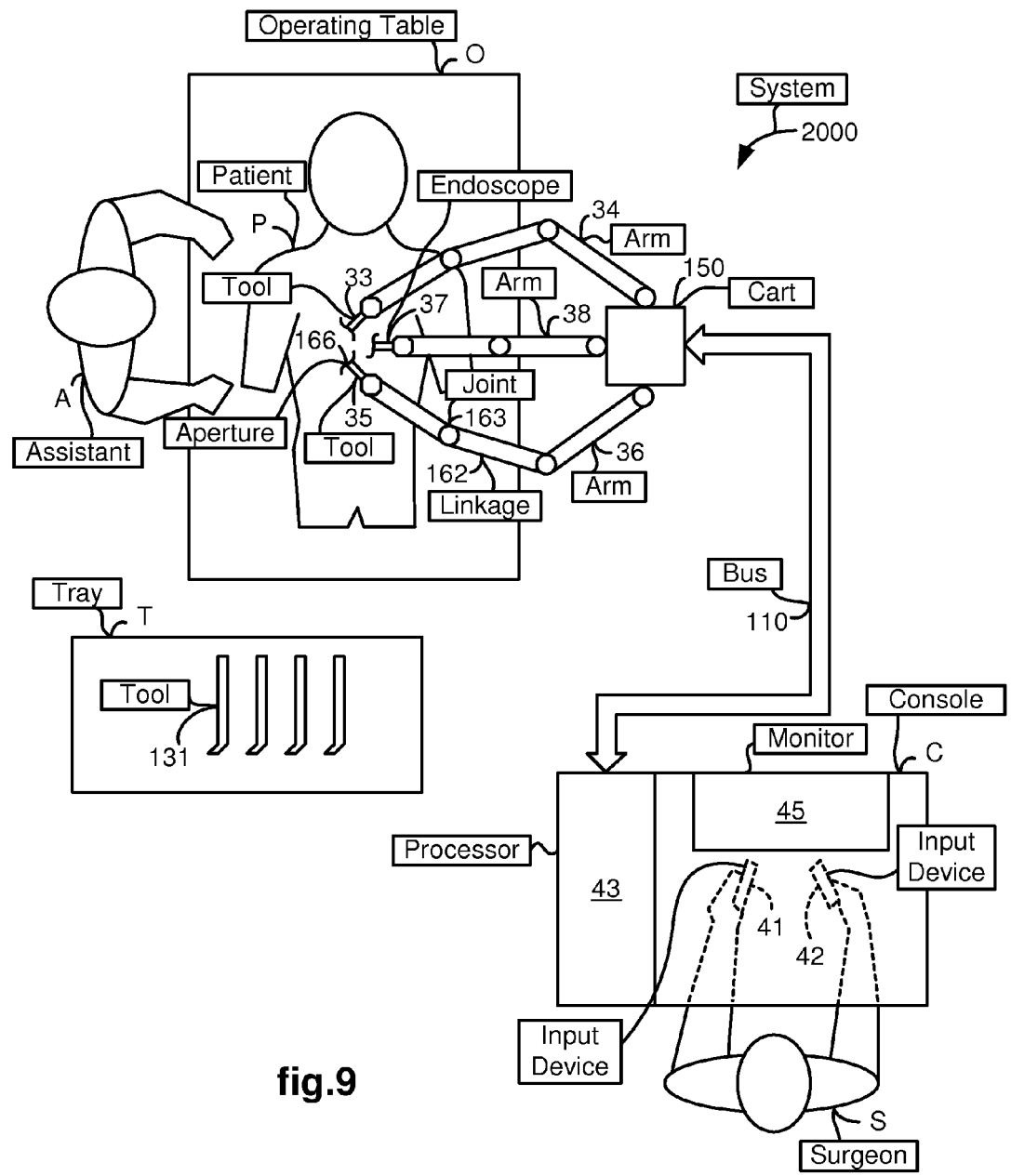
FIG. 9 illustrates a top view of an operating room employing a multiple aperture medical robotic system utilizing aspects of the present invention.
Figure 10:
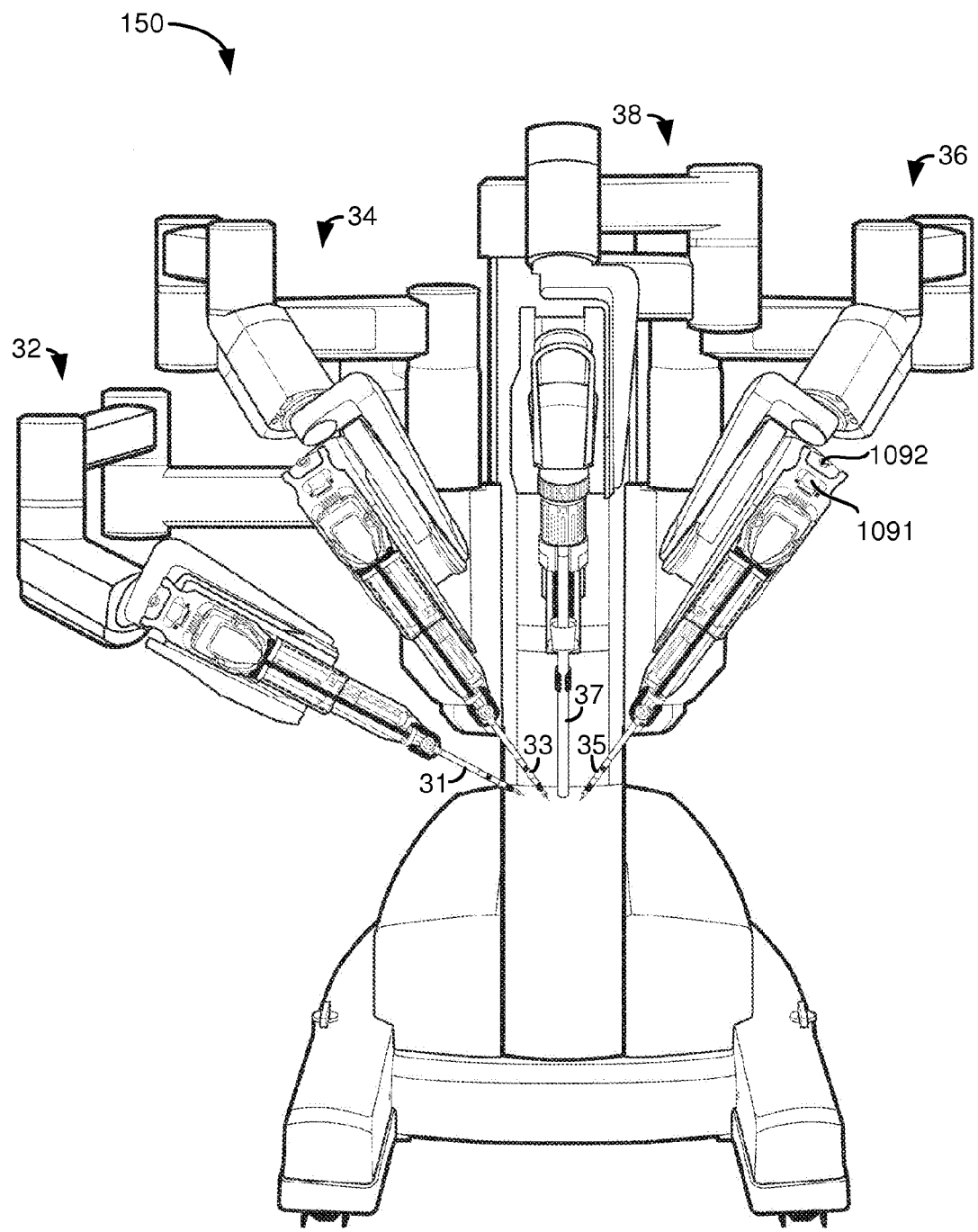
FIG. 10 illustrates a front view of a patient side cart for a multiple aperture medical robotic system utilizing aspects of the present invention.
Figure 11:
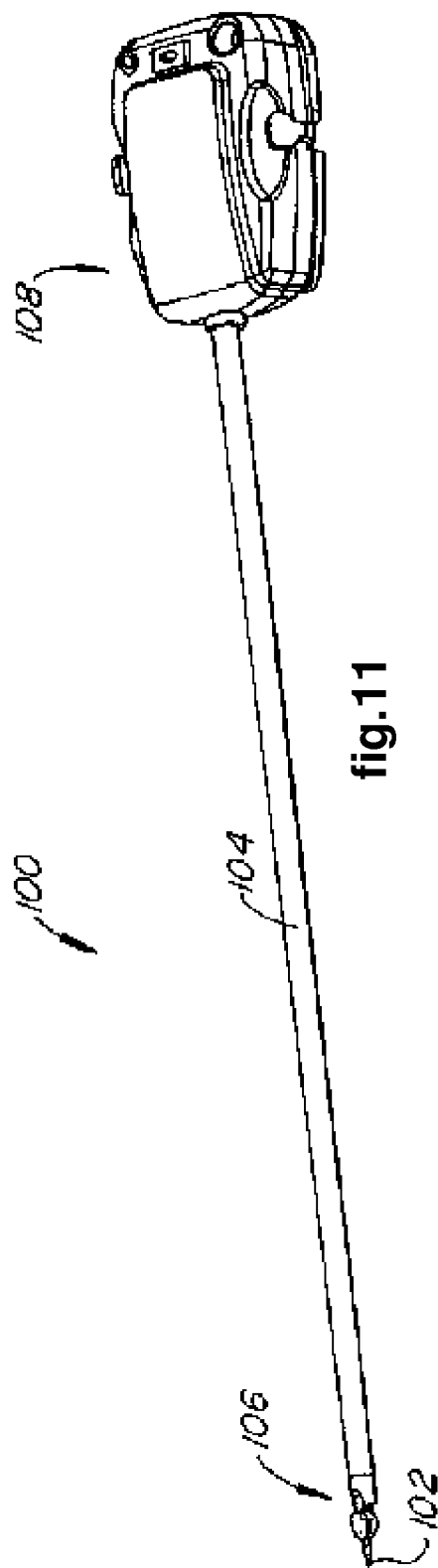
FIG. 11 illustrates a perspective view of an instrument usable in a multiple aperture medical robotic system utilizing aspects of the present invention.

FIG. 1 illustrates, as an example, a block diagram of various components used by a method implemented in a robotic system 1000 for switching control of an instrument (also referred to as a "tool") to an input device upon the instrument entering a display area viewable by an operator of the input device. FIGS. 2-8 illustrate flow charts and other items describing the method. FIGS. 9-11 illustrate details of a first exemplary robotic system 2000 using multiple apertures for entry to a work site. FIGS. 12-15 illustrate details of a second exemplary robotic system 3000 using a single aperture for entry to a work site. FIG. 16 illustrates an exemplary operator's console that may be used with both of the robotic systems 2000 and 3000.

Before describing details of the invention as illustrated in FIGS. 1-8, the exemplary robotic systems 2000 and 3000 will first be described to provide context and additional details on exemplary implementations of the robotic system 1000. Although medical robotic systems are described herein as examples of the robotic system 1000, it is to be appreciated that the various aspects of the invention as claimed herein are not to be limited to such types of robotic systems.

Referring to FIG. 9, a top view of an operating room is illustrated in which a multiple aperture medical robotic system 2000 is being employed by a Surgeon ("S") to perform a medical procedure on a Patient ("P"). The medical robotic system in this case is a Minimally Invasive Robotic Surgical (MIRS) system including a Console ("C") utilized by the Surgeon while performing a minimally invasive diagnostic or surgical procedure on the Patient with assistance from one or more Assistants ("A") while the Patient is on an Operating table ("O").

The Console, as further described in reference to FIG. 16, includes a processor 43 which communicates with a patient-side cart 150 over a bus 110. A plurality of robotic arms 34, 36, 38 are included on the cart 150. An instrument 33 is held and manipulated by robotic arm 34, another instrument 35 is held and manipulated by robotic arm 36, and an endoscope 37 is held and manipulated by robotic arm 38. The medical robotic system 2000 is referred to as being a multiple aperture medical robotic system, because multiple apertures are used so that each of its instruments is introduced through its own entry aperture in the Patient. As an example, instrument 35 is inserted into aperture 166 to enter the Patient.

The Surgeon performs the medical procedure by manipulating the input devices 41, 42 so that the processor 43 causes their respectively associated robotic arms 34, 36 to manipulate their respective removably coupled instruments 33, 35 accordingly while the Surgeon views real-time images of a work site in three-dimensions ("3D") on a stereo vision display 45 (also referred to as "display screen") of the Console. A stereoscopic endoscope 37 (having left and right cameras for capturing left and right stereo views) captures stereo images of the work site. The processor 43 processes the stereo images so that they may be properly displayed on the stereo vision display 45.

Each of the robotic arms 34, 36, 38 is conventionally formed of links, such as link 162, which are coupled together and manipulated through actuatable joints, such as joint 163. Each of the robotic arms includes a setup arm and an instrument manipulator. The setup arm positions its held instrument so that a pivot point occurs at its entry aperture into the Patient. The instrument manipulator may then manipulate its held instrument so that it may be pivoted about the pivot point, inserted into and retracted out of the entry aperture, and rotated about its shaft axis. The robotic arms 34, 36, 38 may be carted into the operating room via a Patient-Side Cart 150 or alternatively, they may be attached to sliders on a wall or ceiling of the operating room.

FIG. 10 illustrates a front view of an exemplary Patient-Side Cart 150. In addition to the robotic arms 34, 36, 38, shown in FIG. 9, a fourth robotic arm 32 is shown in FIG. 10. The fourth robotic arm 32 is available so that another instrument 31 may be introduced at the work site along with the instruments 33, 35 and endoscope 37. Each of the robotic arms 32, 34, 36, 38 may be adapted with a Light Emitting Diode ("LED") array 1091 or other visual indicator to indicate status and/or other information for or related to the robotic arm. One or more buttons 1092 or other type of switch mechanism may also be provided on or near the robotic arm for various purposes such as to allow the Assistant to take control of the robotic arm so that the Assistant may manually retract and/or insert an instrument held by the robotic arm out of or into a corresponding entry aperture in the Patient.

FIG. 11 illustrates an exemplary instrument 100 that may be used for either instrument 33 or 35. The instrument 100 comprises an interface housing 108, a shaft 104, an end effector 102, and a wrist mechanism 106 which includes one or more wrist joints. The interface housing 108 is removably attached to a robotic arm so as to be mechanically coupled to actuators (such as motors) in the instrument manipulator of the attached robotic arm. Cables or rods, that are coupled to the actuators of the instrument manipulator and extend through the shaft 104 from the interface housing 108 to the one or more wrist joints of the wrist mechanism 106 and to the jaws of the instrument's end effector 102, actuate the wrist joints and jaws in a conventional manner. The instrument manipulator may also manipulate the instrument in pitch and yaw angular rotations about its pivot point at the entry aperture, manipulate the instrument in a roll angular rotation about the instrument's shaft axis, and insert and retract the instrument along a rail on the robotic arm as commanded by the processor 43.

The number of surgical tools used at one time and consequently, the number of robotic arms being used in the system 2000 will generally depend on the diagnostic or surgical procedure and the space constraints within the operating room, among other factors. If it is necessary to change one or more of the tools being used during a procedure, the Surgeon may instruct the Assistant to remove the instrument that is no longer being used from its robotic arm, and replace it with another instrument 131 from a Tray ("T") in the operating room. To aid the Assistant in identifying the instrument to be replaced, one or more LEDs of the LED color array 1091 on the robotic arm holding the instrument may be lit. Likewise, to aid the Assistant in identifying the replacement instrument 131, an LED that is adjacent the replacement instrument may be energized. Alternatively, other well known means for conveying such information may be used such as providing the information on a local display screen viewable by the Assistant or by voice instructions to the Assistant from the Surgeon over an audio communication system. To transfer control of the instrument (and its manipulator) from the Surgeon to the Assistant, either the Surgeon may activate a button on or adjacent to the input device associated with the instrument (such as button 49 adjacent the input device 42 as seen in FIG. 16), or alternatively, the Assistant may activate a button such as the mechanism 1092 on the robotic arm holding the instrument. After the Assistant is in control of the instrument, the Assistant may then retract the instrument out of the Patient by manually sliding it backwards along the rail on its robotic arm or insert the instrument into the Patient by manually sliding it forward along the rail.

U.S. Pat. No. 6,659,939 B2 entitled "Cooperative Minimally Invasive Telesurgical System," which is incorporated herein by reference, provides additional details on a multiple aperture medical robotic system such as described herein.

Figure 12:
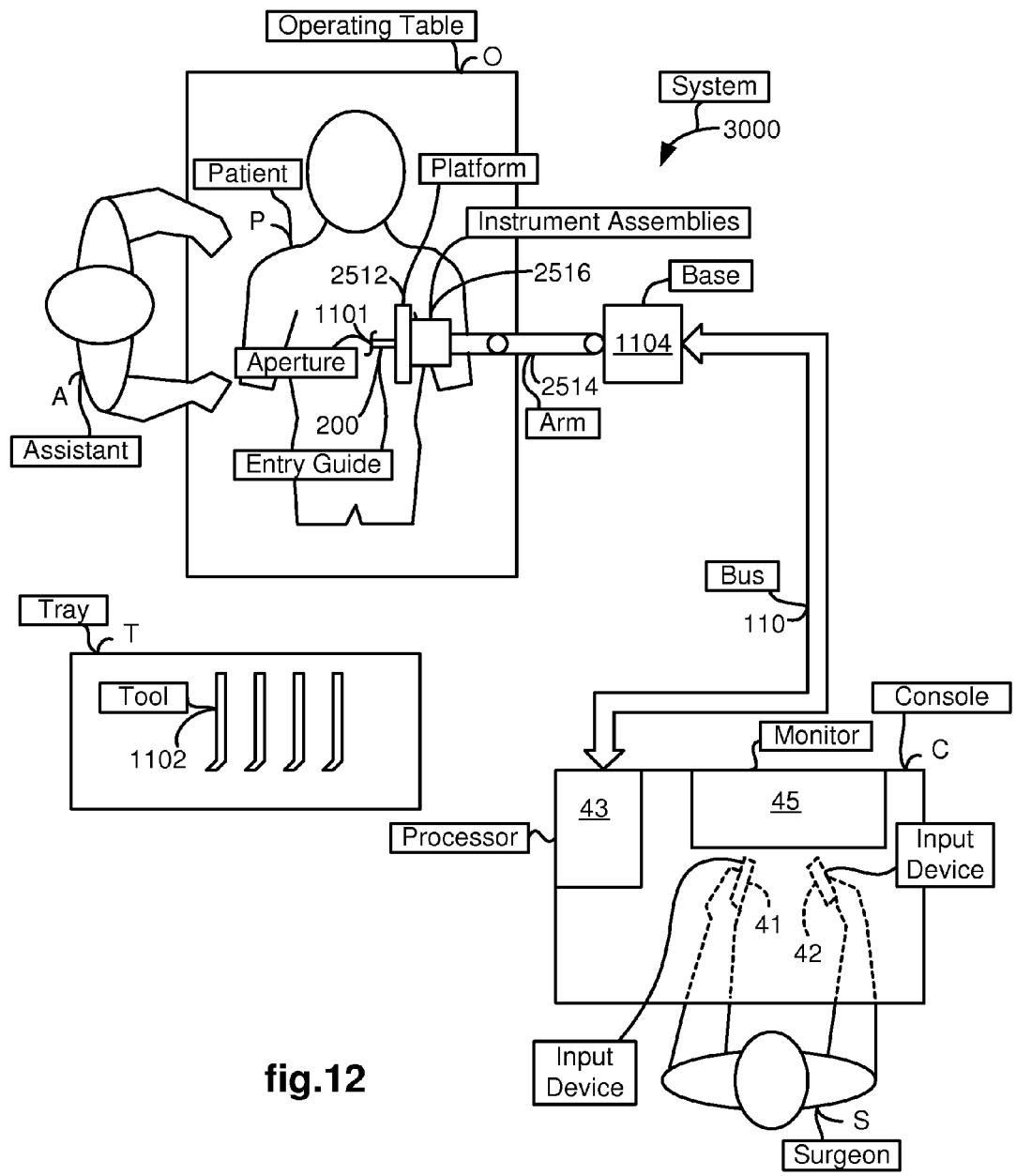
FIG. 12 illustrates a top view of an operating room employing a single aperture medical robotic system utilizing aspects of the present invention.

As a second example of the robotic system 1000, FIG. 12 illustrates a top view of an operating room in which a single aperture medical robotic system 3000 is being employed by a Surgeon ("S") to perform a medical procedure on a Patient ("P"). The medical robotic system in this case is a Minimally Invasive Robotic Surgical (MIRS) system including a Console ("C") utilized by the Surgeon while performing a minimally invasive diagnostic or surgical procedure on the Patient with assistance from one or more Assistants ("A") while the Patient is on an Operating table ("O").

In the single aperture medical robotic system 3000, a plurality of articulated instruments are introduced to a work site through a single entry aperture 1101 in the Patient by an entry guide (EG) 200. The aperture 1101 may be a minimally invasive incision or a natural body orifice. The entry guide 200 is a cylindrical structure which is held and manipulated by a robotic arm 2514. The robotic arm 2514 includes a setup arm and an entry guide manipulator. The setup arm is used to position the entry guide 200 at the aperture 1101 so that a pivot point occurs at the aperture. The entry guide manipulator may then be used to robotically insert and retract the entry guide 200 into and out of the aperture 1101. It may also be used to robotically pivot the entry guide 200 (and the articulated instruments disposed within it at the time) in pitch and yaw angular rotations about the pivot point. It may also rotate the entry guide 200 (and the articulated instruments disposed within it at the time) in roll about a longitudinal axis of the entry guide 200. Attached to the distal end of the robotic arm 2514 is a platform 2512 upon which instrument assemblies 2516 are mounted so that their respective instruments may extend through the entry guide 200. Each instrument assembly comprises an articulated instrument and its instrument manipulator.

Figure 13:
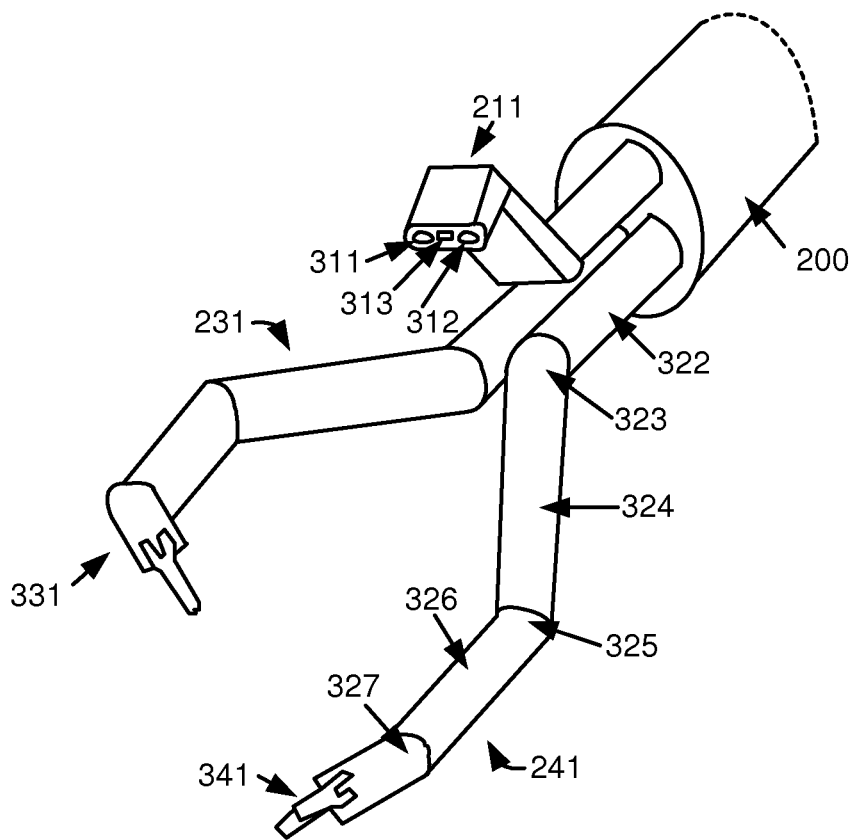
FIG. 13 illustrates a perspective view of a distal end of an entry guide with articulated instruments extending out of it in a single aperture medical robotic system utilizing aspects of the present invention.
Figure 14:
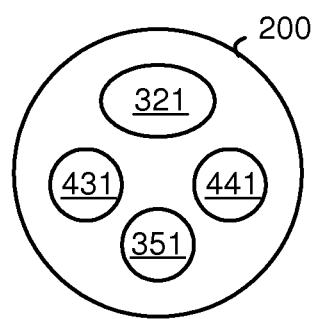
FIG. 14 illustrates a cross-sectional view of an entry guide useful in a single aperture medical robotic system utilizing aspects of the present invention.

As shown in FIG. 13, the entry guide 200 has articulated instruments such as articulated surgical tool instruments 231, 241 and an articulated stereo camera instrument 211 (or other image capturing device instrument) extending out of its distal end. The camera instrument 211 has a pair of stereo image capturing devices 311, 312 and a fiber optic cable 313 (coupled at its proximal end to a light source) housed in its tip. The surgical tools 231, 241 have end effectors 331, 341. Although only two tools 231, 241 are shown, the entry guide 200 may guide additional tools as required for performing a medical procedure at a work site in the Patient. For example, as shown in a cross-sectional view of the entry guide 200 in FIG. 14, a passage 351 is available for extending another articulated surgical tool through the entry guide 200 and out through its distal end. Passages 431, 441, are respectively used by the articulated surgical tool instruments 231, 241, and passage 321 is used for the articulated camera instrument 211.

Each of the articulated instruments comprises a plurality of actuatable joints and a plurality of links coupled to the joints. As an example, as shown in FIG. 13, the second articulated instrument 241 comprises first, second, and third links 322, 324, 326, first and second joints 323, 325, and a wrist assembly 327. The first joint 323 couples the first and second links 322, 324 and the second joint 325 couples the second and third links 324, 326 so that the second link 324 may pivot about the first joint 323 in pitch and yaw while the first and third links 322, 326 remain parallel to each other. The first, third, and camera articulated instruments, 231, 251, 211, may be similarly constructed and operated.

Figure 15:
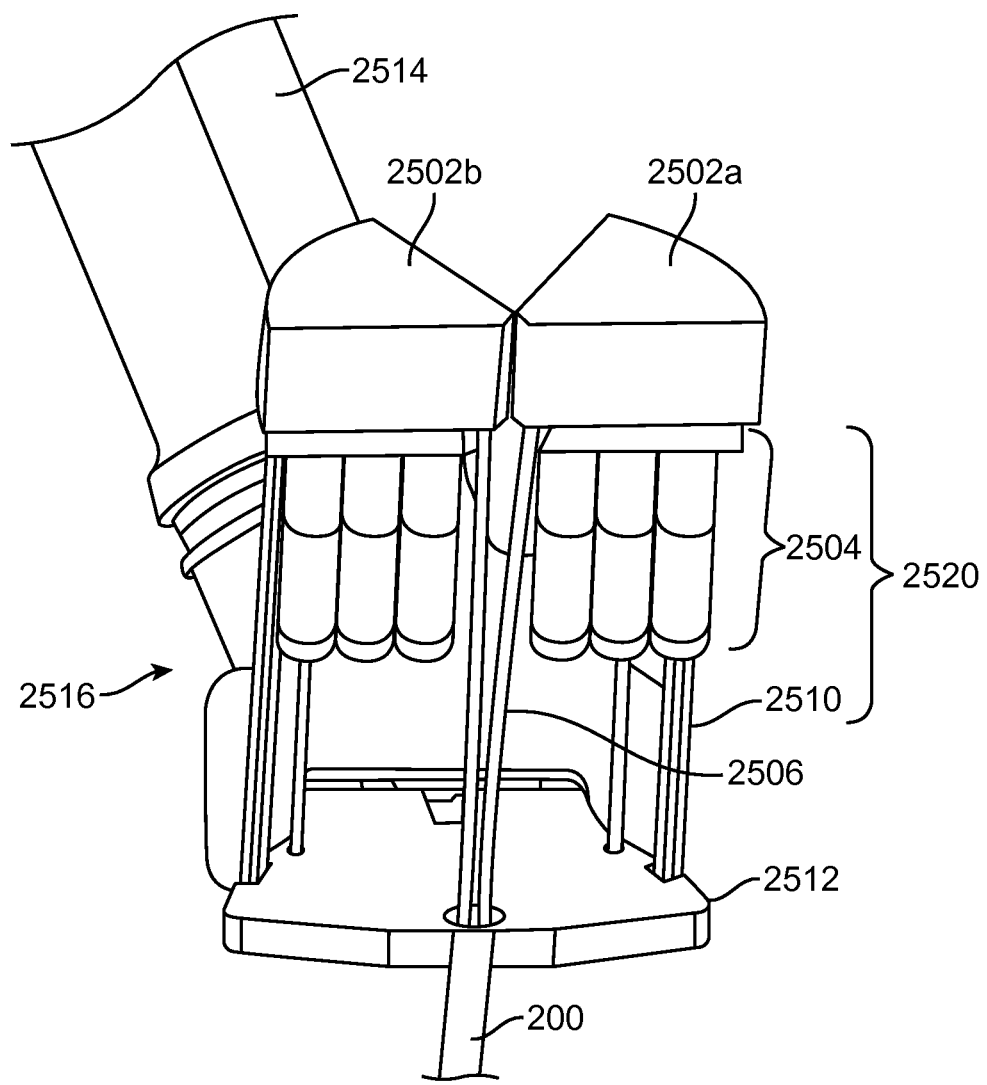
FIG. 15 illustrates a perspective view of articulated instrument assemblies mounted on a platform coupled to a robotic arm assembly in a single aperture medical robotic system utilizing aspects of the present invention.
Figure 16:
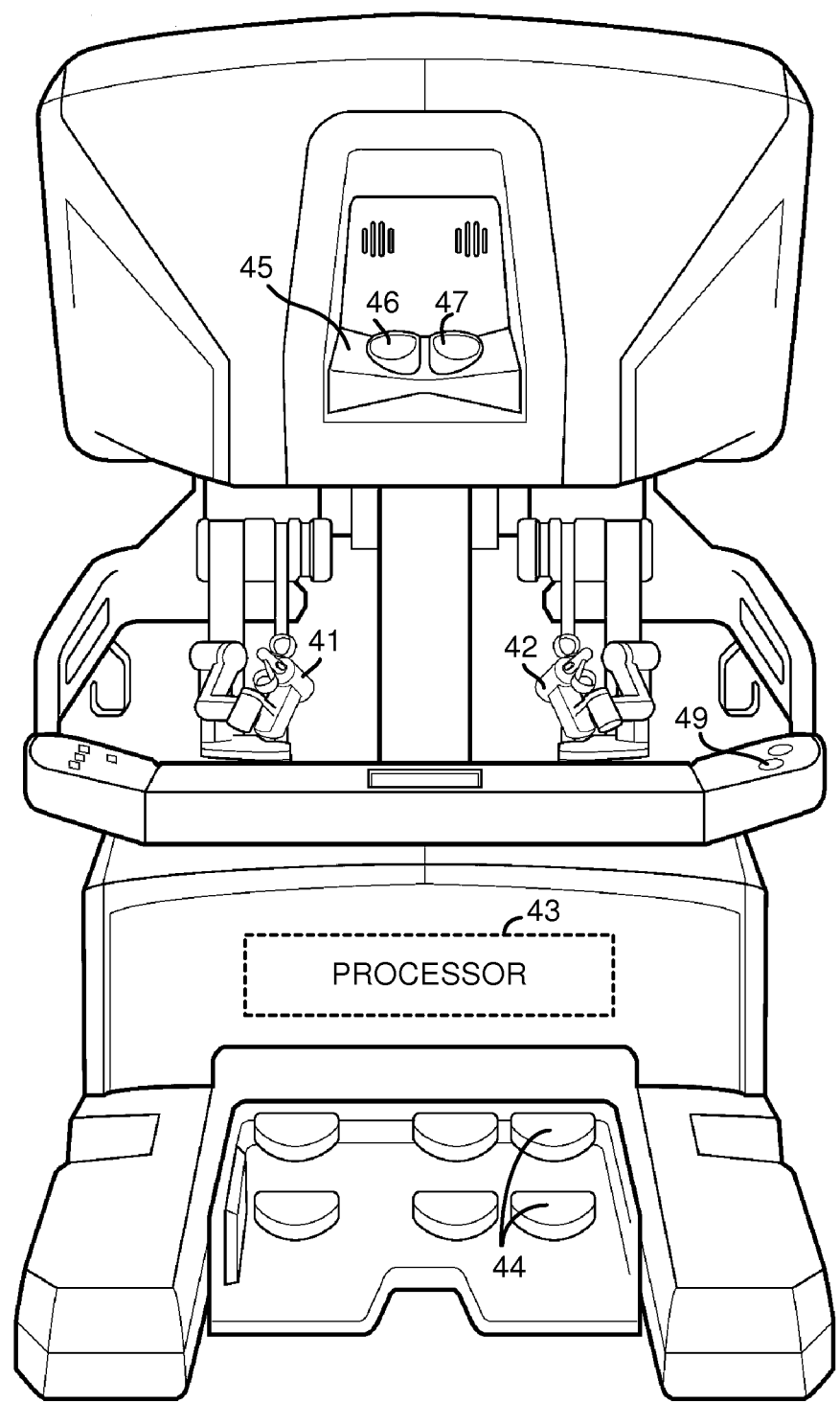
FIG. 16 illustrates a front view of a console usable in a robotic system utilizing aspects of the present invention.

FIG. 15 illustrates, as an example, articulated instrument assemblies 2516 mounted on a platform 2512 at a distal end of the robotic arm 2514. The entry guide 200 is attached to the platform 2512 so that entry guide 200 may be manipulated (along with the platform 2512) by the entry guide manipulator, as previously described. Each articulated instrument assembly includes an articulated instrument and its instrument manipulator. For example, an exemplary articulated instrument 2502a is mounted on an actuator assembly 2504 which includes a plurality of actuators for actuating joints of the articulated instrument. Instrument 2502a has a body tube 2506 that extends past its actuator assembly 2504 and enters the entry guide 200. Actuator assembly 2504 is mounted to a linear actuator 2510 (e.g. a servocontrolled lead screw and nut or a ball screw and nut assembly) that controls the insertion and retraction of the body tube 2506 into and out of the entry guide 200. The instrument manipulator 2520 in this case comprises the actuator assembly 2504 and the linear actuator 2510. In the case where the instrument 2502a is the articulated instrument 241, the distal end of the body tube 2506 is the first link 322 shown in FIG. 13. The second instrument 2502b is mounted with similar mechanisms as shown. In addition, an articulated camera instrument may be similarly mounted.

FIG. 16 illustrates, as an example, a front view of a Console which may used in both medical robotic systems 2000 and 3000. The Console has left and right input devices 41, 42 which the user may grasp respectively with his/her left and right hands to manipulate associated devices, such as the entry guide and articulated instruments, in preferably six degrees-of-freedom ("DOF"). Foot pedals 44 with toe and heel controls are provided on the Console so the user may control movement and/or actuation of devices associated with the foot pedals. A processor 43 is provided in the Console for control and other purposes. A stereo vision display 45 is also provided in the Console so that the user may view the work site in stereo vision from images captured by the stereoscopic camera of the endoscope 37 or the articulated camera instrument 211. Left and right eyepieces, 46 and 47, are provided in the stereo vision display 45 so that the user may view left and right two-dimensional ("2D") display screens inside the display 45 respectively with the user's left and right eyes.

The processor 43 performs various functions in the medical robotic system. One important function that it performs is to translate and transfer the mechanical motion of input devices 41, 42 through control signals over bus 110 to command actuators in their associated manipulators to actuate their respective joints so that the Surgeon can effectively manipulate devices, such as the tool instruments 231, 241, camera instrument 211, and entry guide 200. Another function is to perform various methods described herein.

Although described as a processor, it is to be appreciated that the processor 43 may be implemented by any combination of hardware, software and firmware. Also, its functions as described herein may be performed by one unit or divided up among different components, each of which may be implemented in turn by any combination of hardware, software and firmware. Further, although being shown as part of or being physically adjacent to the Console, the processor 43 may also comprise a number of subunits distributed throughout the system.

U.S. Publication No. US 2008/0065108 A1 entitled "Minimally Invasive Surgical System," which is incorporated herein by reference, provides additional details on a single aperture medical robotic system such as described herein.

Now referring back to FIG. 1, a block diagram of components of the robotic system 1000 is illustrated to describe various aspects of the present invention. In this example, the robotic system 1000 has two tools and one camera. The pose (i.e., position and orientation) of the working end of the first tool is movable by a first plurality of actuatable joints 1001 whose positions and/or velocities are sensed by a first plurality of joint sensors 1002, the pose of the working end of the second tool is movable by a second plurality of actuatable joints 1004 whose positions and/or velocities are sensed by a second plurality of joint sensors 1005, and the pose of the image capturing end of the camera 37 is movable by a third plurality of actuatable joints 1007 whose positions and/or velocities are sensed by a third plurality of joint sensors 1008. Images captured by the camera 37 are processed by a video processor 1010 and/or the processor 43 with the processed images displayed on the stereo vision display 45.

In a normal operating mode (referred to as a "tool following" mode), an operator of the system 1000 controls the tools to perform a procedure on an object at a work site while an on-site camera captures images of the working ends of the tools. In this mode, the input device 41 is associated with the first tool so that the processor 43 causes a first plurality of joint actuators 1003 to actuate the first plurality of joints 1001 so that sensed joint positions and/or velocities provided by the first plurality of joint sensors 1002 match the joint positions and/or velocities commanded at the time by the input device 41. Also, input device 42 is associated with the second tool so that the processor 43 causes a second plurality of joint actuators 1006 to actuate the second plurality of joints 1004 so that sensed joint positions and/or velocities provided by the second plurality of joint sensors 1005 match the joint positions and/or velocities commanded at the time by the input device 42. Meanwhile, the camera 37 may be held in place by the processor 43 commanding a third plurality of joint actuators 1009 to maintain the third plurality of joints 1007 in their current positions. Alternatively, the camera 37 may track movement of the first and second tools by the processor 43 commanding the third plurality of joint actuators 1009 to actuate the third plurality of joints 1007 so that the working ends of the first and second tools remain in a field-of-view ("FOV") of the camera 37.

One or more switches 1011 are provided to indicate that control of one of the tools is to be switched to an assistant operator or the processor 43. Some or all of the switches 1011 may be provided on the robotic arms holding the tools so that the assistant may activate a designated one of the switches and assume control of the corresponding tool through the processor 43. Alternatively or additionally, some or all of the switches 1011 may be provided on or adjacent to the input devices 41, 42 (such as the switch 40 on an arm rest as shown in FIG. 16) so that the operator may activate a designated one of the switches and transfer control of the associated tool to the assistant through the processor 43 for manual action or directly to the processor 43 for automated action. One or more indicators 1012 (such as LEDs) are also provided to indicate to the assistant which one of the tools whose control is being switched to the assistant by the processor 43. One or more of the indicators 1012 may be provided on the robotic arms holding the tools so that the assistant knows which one of the tools is now under his or her control. Additionally, one or more of the indicators 1012 may be provided on a structure so that a tool may be indicated by the processor 43 as a new or replacement tool to be introduced to the work site. A memory 1013 is provided to store programmed instructions and data.

Figure 2:
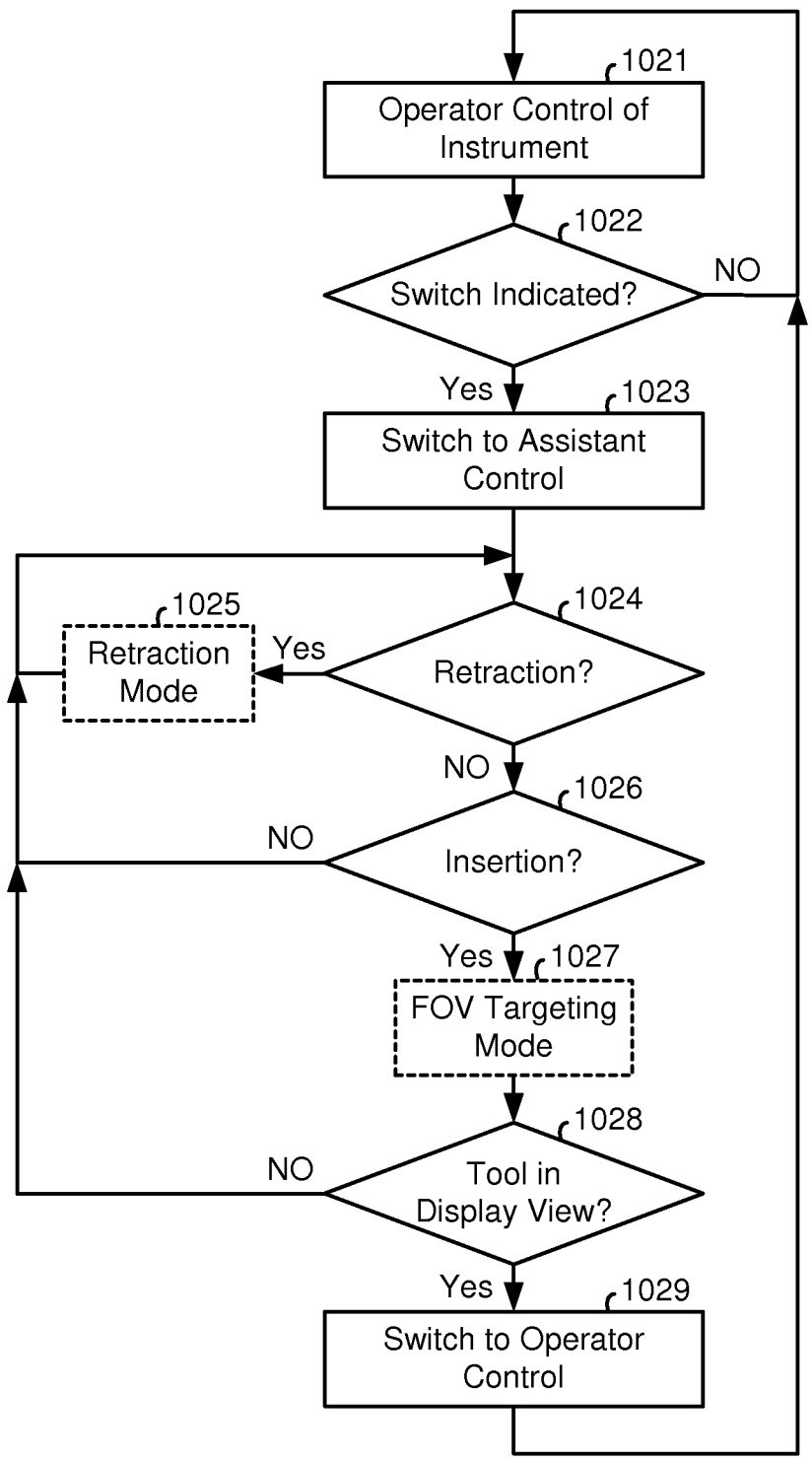
FIG. 2 illustrates a flow diagram of a method of switching control of an instrument to an input device utilizing aspects of the present invention.

FIG. 2 illustrates a flow diagram of a method implemented in the processor 43 of the robotic system 1000 for switching control of an instrument to an input device. In block 1021, the operator is operating in a normal mode in which the operator has control of an instrument through its associated input device, as described previously. In block 1022, the method checks whether control of the instrument is to be switched to the assistant so that the assistant may manually control its movement by moving its manipulator or to the processor 43 so that the processor may control its movement according to programmed instructions. As previously described, such switching may be indicated by activation of one of the switches 1010. If the determination in block 1022 is NO, then the method jumps back to block 1021 and the operator maintains control of the instrument. On the other hand, if the determination in block 1022 is YES, then in block 1023, the method switches control of the instrument to the assistant or processor 43.

In blocks 1024 and 1026, the method respectively determines whether the instrument is moving in a retraction direction or an insertion direction. If the instrument is moving in a retraction direction (i.e., in a direction that would result in the instrument moving away from the work site), then the method allows such action and either loops back to repeat block 1024 or performs an optional block 1025 to perform a retraction mode algorithm that commands an articulated instrument to assume a retraction pose and/or avoid collisions with other instruments or objects during the instrument's retraction. Additional details for such a retraction algorithm for an articulated instrument may be found, for example, in U.S. Publication No. US 2011/0040305 A1 entitled "Controller Assisted Reconfiguration of an Articulated Instrument during Movement Into and Out of an Entry Guide," which is incorporated herein by reference. On the other hand, if the instrument is moving in an insertion direction (i.e., in a direction moving towards the work site), then the method allows such action and either proceeds directly to block 1028 or performs an optional block 1027 in which a camera field of view (FOV) targeting algorithm commands the tool joint actuators to actuate the tool joints so that the working end of the instrument moves towards the FOV of the camera 37 while avoiding collisions with other instruments and objects on the way. In this way, if the camera 37 moves during the procedure, the working end of the instrument may automatically change its direction to follow it as it is being inserted towards the work site.

The camera 37 may move during the procedure if a coupled control mode is implemented by the processor 43 in which the pose of the camera 37 is automatically changed in response to commanded movement of the instruments so that the working ends of the instruments are maintained in the field of view of the camera 37. The camera 37 may move in response to direct operator commands through an associated input device. In this latter case, the operator may effectively guide the placement of the instrument being inserted by the assistant to a desired location at the work site.

Figure 7A:
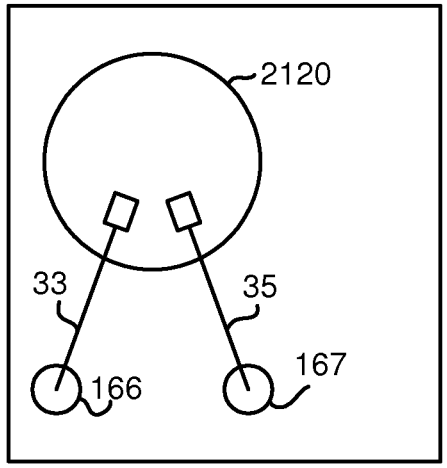
FIGS. 7a-7d illustrate schematic views of instruments at a work site in various stages of a guided tool exchange procedure performed in a multiple aperture medical robotic system utilizing aspects of the present invention.
Figure 7B:
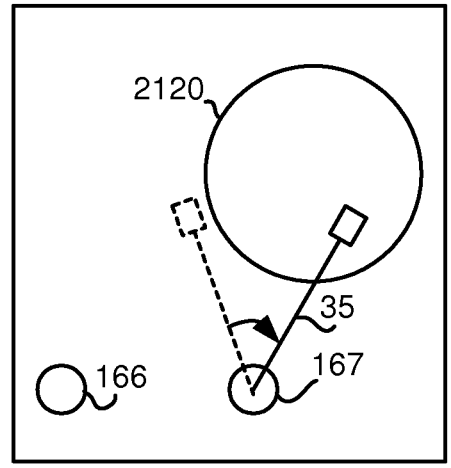
Figure 7C:
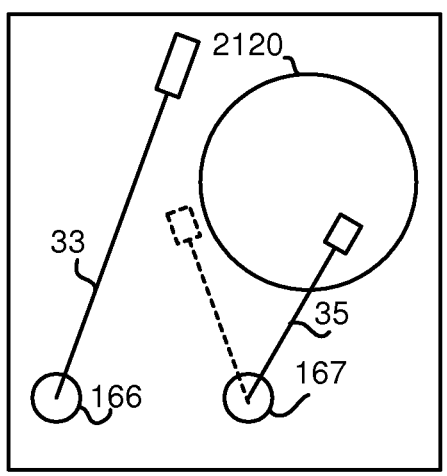
Figure 7D:
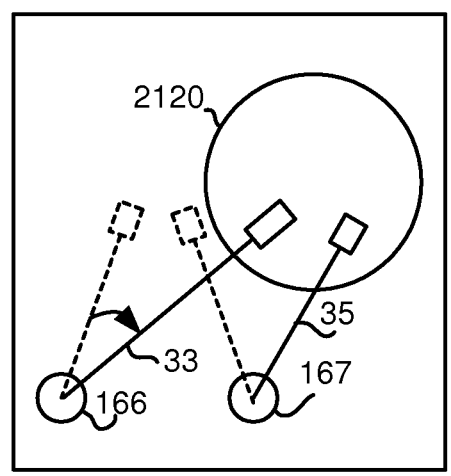

As a simplified example of the FOV targeting algorithm, FIGS. 7a-7d illustrate schematic views of instruments 33, 35 extending out of their respective apertures 166, 167 at a work site in various stages of a guided tool exchange procedure using the multiple aperture medical robotic system 2000. In FIG. 7a, the working ends of the instruments are shown as being in a field of view (FOV) 2120 of the endoscope 37. In FIG. 7b, three events have occurred since the time corresponding to FIG. 7a. First, instrument 33 has been retracted for a tool exchange so the instrument 33 is not seen in this figure. Second, the working end of instrument 35 has moved as indicated by the instrument's prior position in dotted line form and new position in solid line form with an arrow indicating the direction of the movement. Third, the image capturing end of the endoscope 37 and its FOV 2120 has also moved to maintain the working end of the instrument 35 in the camera's FOV 2120. In FIG. 7c, the instrument 33 (or its replacement) has been reinserted along a line extending through its original retraction path. Since the FOV 2120 of the endoscope 37 has moved, however, the working end of the instrument 33 does not enter the FOV 2120 in this case. Therefore, to prevent this situation from occurring, in FIG. 7d, the FOV targeting algorithm has caused the instrument 33 to be pivoted during its insertion so that the working end of the instrument 33 is in the repositioned FOV 2120. The pivoting in this case is illustrated by showing the instrument's original position in dotted line form and modified position in solid line form with an arrow indicating the direction of the pivoting performed in response to the insertion mode algorithm. As may be appreciated, care must taken during the pivoting of the instrument 33 to avoid collisions with other instruments and/or striking objects at or on the way to the work site. To prevent such misfortune, conventional collision avoidance techniques may be employed by the FOV targeting algorithm using knowledge of the current placements of such objects and the other instruments.

Referring back to FIG. 2, in block 1028, the method determines whether or not the instrument has entered into a view of the work site that is being displayed at the time on the stereo vision display 45. If the determination in block 1028 is NO, then the method jumps back to perform blocks 1024 and 1026 again. On the other hand, if the determination in block 1028 is YES, then in block 1029 the method switches control of the instrument from the assistant back to the operator and loops back to block 1021.

Although not shown in the flow diagram, the method may also be implemented so that either the assistant or the operator may over-ride the flow of FIG. 2 at any time to switch control of the instrument to the operator. For example, one of the switches 1011 may be activated to indicate that the normal process is being interrupted and control of the instrument is to immediately revert back to the operator. One way this may be done is by deactivating the switch that was previously activated to switch control of the instrument from the operator.

Figure 3:
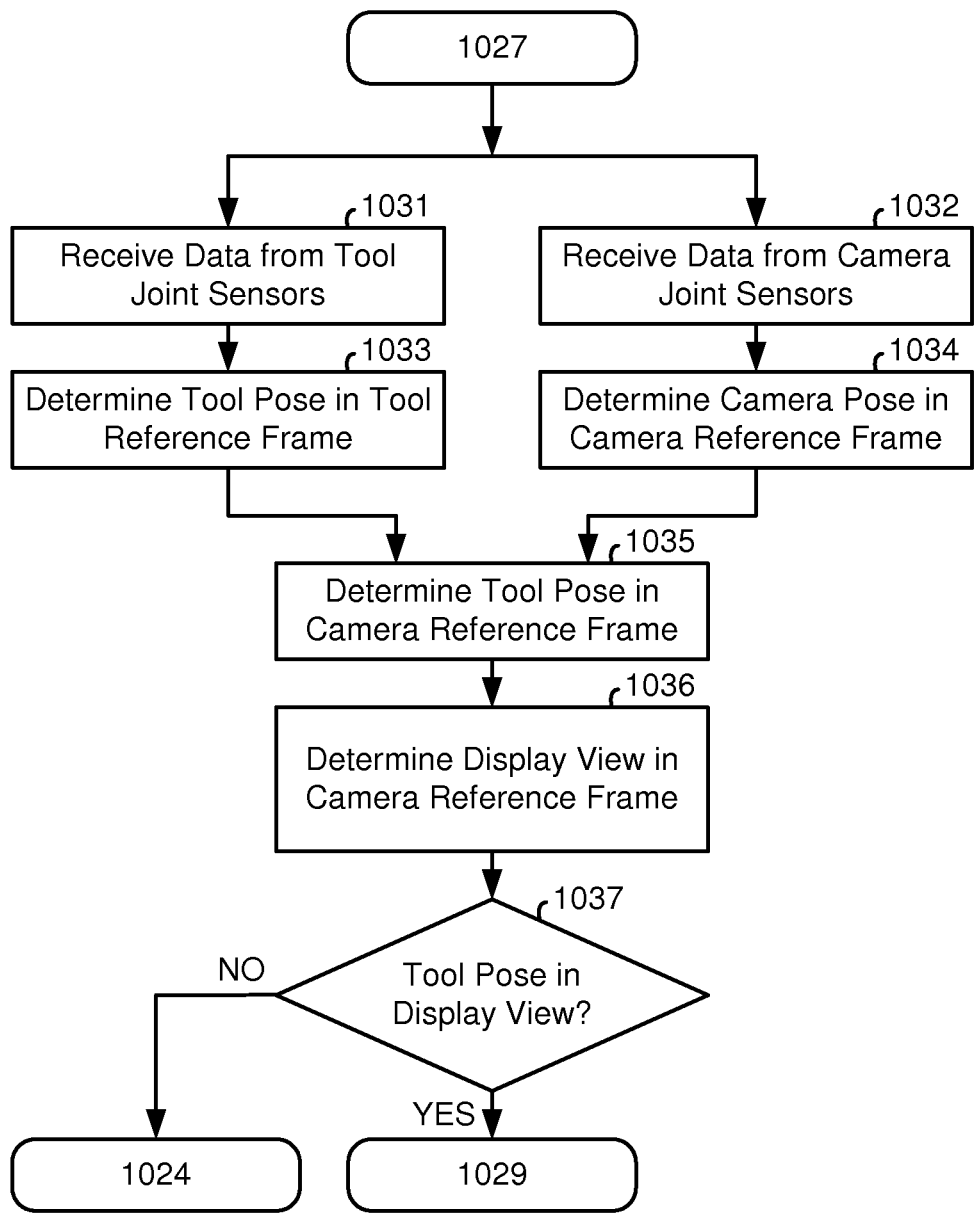
FIG. 3 illustrates a flow diagram of a method for determining whether an instrument is within a viewing area of a display screen, which may be used in the method of FIG. 2 utilizing aspects of the present invention.

FIG. 3 illustrates, as an example, a flow diagram of a method for performing block 1028 of FIG. 2. In block 1031, the method receives data from the tool joint sensors of the instrument currently being controlled by the assistant. Concurrently, in block 1032, the method receives data from the camera joint sensors. In block 1033, the method determines the pose of the working end of the instrument in its tool reference frame by, for example, mapping the tool joint data to a pose in the tool reference frame using an inverse kinematics algorithm for the instrument, wherein the tool reference frame is, for example, a Cartesian reference frame having its origin fixed on a point on the instrument. In block 1034, the method determines the pose of an image capturing end of the camera 37 in its camera reference frame by, for example, mapping the camera joint data to a pose in the camera reference frame using an inverse kinematics algorithm for the camera instrument, wherein the camera reference frame is, for example, a Cartesian reference frame having its origin fixed on a point on the camera instrument.

In block 1035, the method determines the pose of the working end of the instrument in the camera reference frame. It may do this simply by using a known transformation between the tool reference frame and a world reference frame and a known transformation between the camera reference frame and the world reference frame, wherein the world reference frame is, for example, a Cartesian reference frame having its origin at a stationary point at the work site. The determined pose of the working end of the instrument in the camera reference frame may then be corrected using a previously determined error transform, wherein the error transform may be determined from a difference between the tool pose determined using the inverse kinematics algorithm and a tool pose determined using video image processing. The error transform may be first determined with a pre-operative calibration step, and periodically updated when the working end of the instrument is in the field of view of the camera 37. For additional details on such reference frames and transformations, see, for example, U.S. Pat. No. 6,671,581 B2 entitled "Camera Referenced Control in a Minimally Invasive Surgical Apparatus," which is incorporated herein by reference.

In block 1036, the method determines the display view relative to the camera view, wherein the display view is what is being displayed at the time on the stereo vision display 45 and the camera view is the stereo image being captured at the time by the stereo camera.

Figure 4:
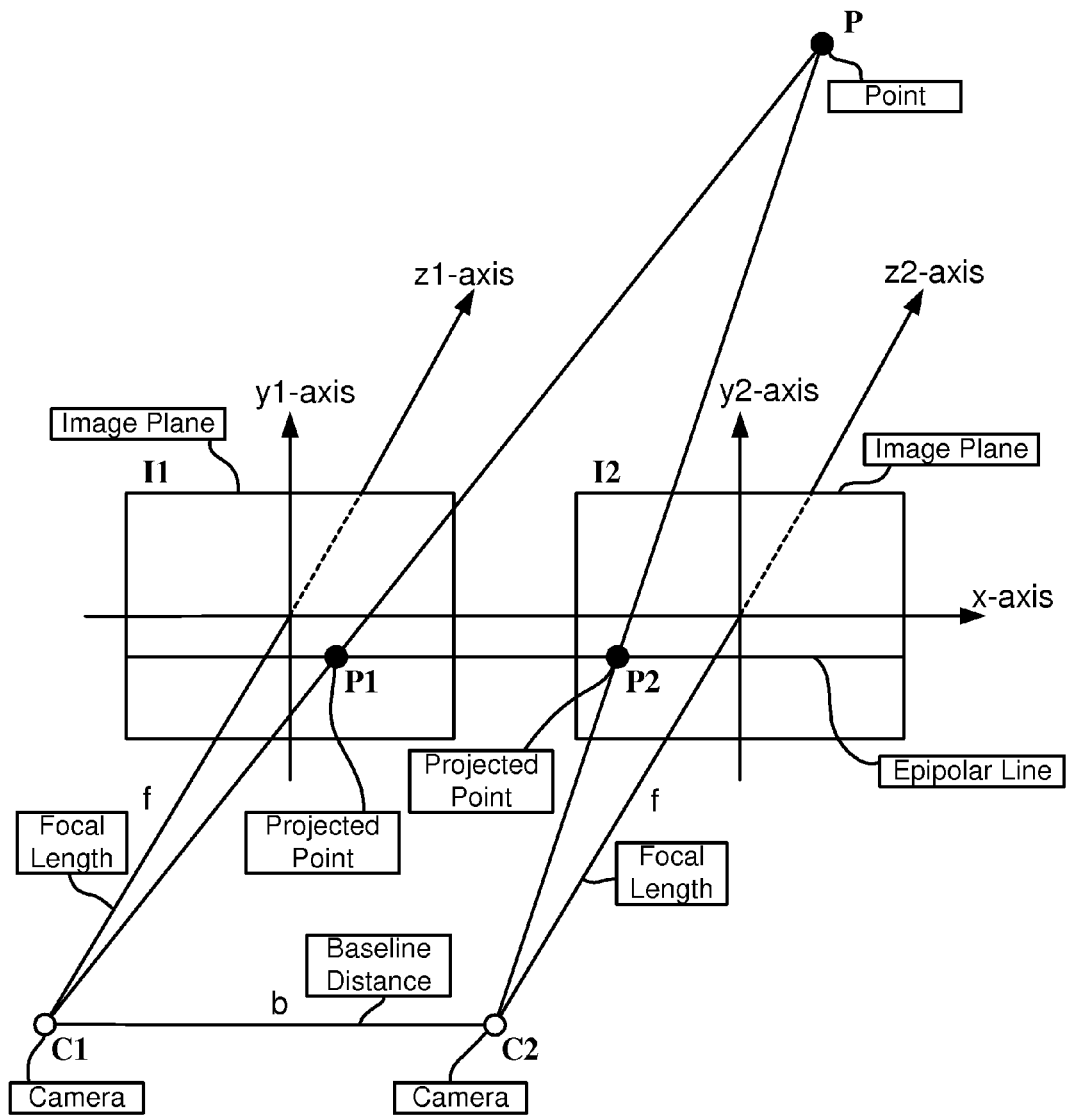
FIG. 4 illustrates left and right views of a point in a camera reference frame.

Referring to FIG. 4, as an illustrative example, the stereo camera includes two cameras, C1 and C2, separated by a baseline distance "b", and having image planes, I1 and I2, defined at the focal length "f" of the cameras. The image planes, I1 and I2, are warped using a conventional stereo rectification algorithm to remove the effects of differing internal and external camera geometries.

A point P in the camera reference frame is projected onto the image planes, I1 and I2, at image points, P1 and P2, by an epipolar plane containing the point P, the two optical centers of the cameras, C1 and C2, and the image points, P1 and P2. The position of the point P may then be determined in the camera reference frame using known values for the baseline distance "b" and focal length "f", and a disparity "d" calculated from the distances of the image points, P1 and P2, from their respective image plane center points (i.e., at the intersections of the x-axis with the y1 and y2 axes).

Figure 5:
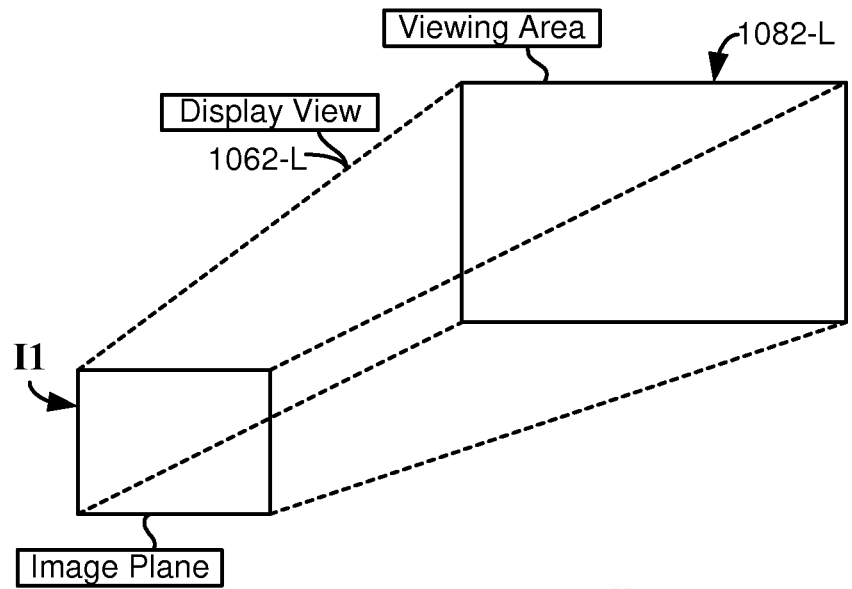
FIGS. 5 and 6 respectively illustrate a full left camera view being displayed on a left viewing area of a computer monitor and partial left camera view being displayed on a left viewing area of a computer monitor.

When the display view is the same as the camera view (i.e., the field of view of the camera), then the left image plane I1 will be displayed in the left eye piece 46 of the stereo display 45 and the right image plane I2 will be displayed in the right eye piece 47 of the stereo display 45. As shown in FIG. 5, the display view in this case for the left eye piece 46 is a frustum of the left camera C1 which emanates from the camera C1 and passes through the left image plane I1 as indicated in the figure as display view 1062-L. A viewing area 1082-L is also shown in FIG. 5 to illustrate the frustum, wherein the viewing area 1082-L is a slice of the frustum that is further away from the camera C1 than the left image plane I1, but parallel to the left image plane I1. The display view for the right eye piece 47 would be a similar frustum emanating from the right image plane I2.

Figure 6:
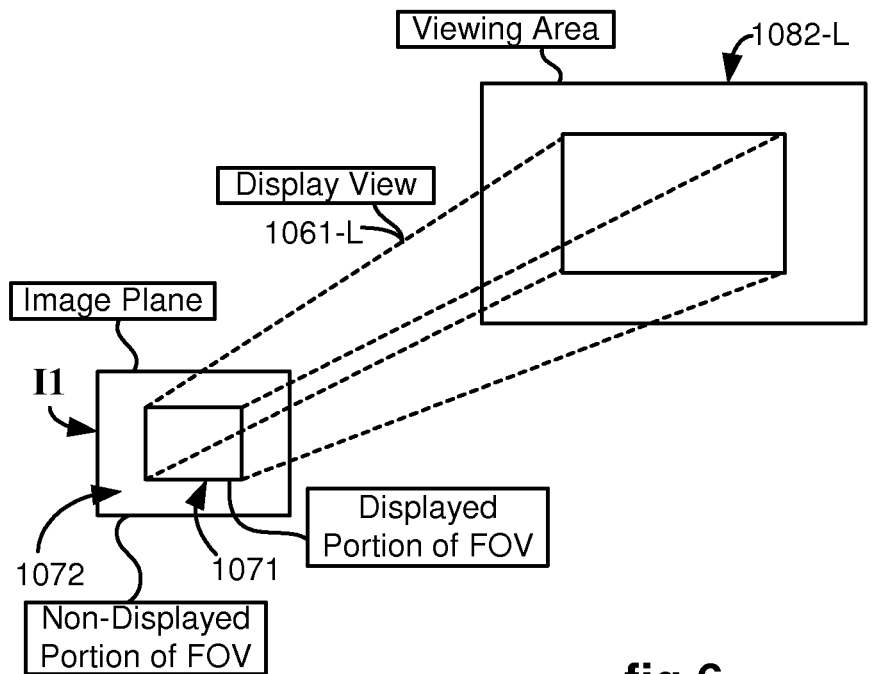

If only a portion of the field of view of the camera 37 is being displayed in the stereo vision display 45, however, such as depicted by area 1071 in FIG. 6, then the display view for the left eye piece 46 is a smaller frustum emanating from the camera C1 as indicated in the figure as display view 1061-L. Such a smaller display view may occur, for example, when the operator commands the stereo vision display 45 to "zoom-in" on images being displayed at the time on the stereo vision display 45. In addition, the processor 43 may further regulate the display view by shifting it to the right or left, shifting it up or down, or rotating it, to provide an intuitive connection in controlling the tools whose images are being seen at the time on the stereo vision display 45 with their associated input devices 41, 42. Although only the left camera view I1 is shown in FIGS. 5 and 6, it is to be appreciated that for a 3-D display, a corresponding right camera view I2 is also necessary such as described in reference to FIG. 4, but is not being shown in FIGS. 5 and 6 to simplify the description. Additional details for a stereo imaging system such as used herein may be found, for example, in U.S. Pat. No. 6,720,988 entitled "Stereo Imaging System and Method for Use in Telerobotic Systems," which is incorporated herein by reference.

Referring back to FIG. 3 now, in block 1037, the method then determines whether the pose of the working end of the instrument (which was determined in block 1035) is at least partially in the display view (which was determined in block 1036). If the determination in block 1037 is NO, then the method jumps back to block 1024 as shown in FIG. 2. On the other hand, if the determination in block 1037 is YES, then the method proceeds to block 1029 as shown in FIG. 2. As a refinement to simply using the kinematically determined pose of the working end of the instrument in block 1037, a computer model of the working end may also be used as a template to identify the working end in the left and right images being displayed at the time in the left and right eye pieces 46, 47 of the stereo vision display 45. The image matching in this case may be performed only after the kinematically determined pose of the working end of the instrument has reached a threshold distance from the display view in order to save the processor 43 from performing unnecessary processing.

During the insertion of the instrument, it is desirable to specify a "target location" for the instrument by specifying minimum and maximum insertion distances. As an example, FIG. 8a illustrates a simplified schematic view of the articulated tool instruments 231, 241 and articulated camera instrument 211 extending out of a distal end of the entry guide 200 in the single aperture medical robotic system 3000. In this schematic, an object 500 and field of view (FOV) 2110 of the camera 211 are also shown. For descriptive purposes, the FOV 2110 is also assumed to be the display view for the purposes of block 1028 in FIG. 2.

Figure 8B:
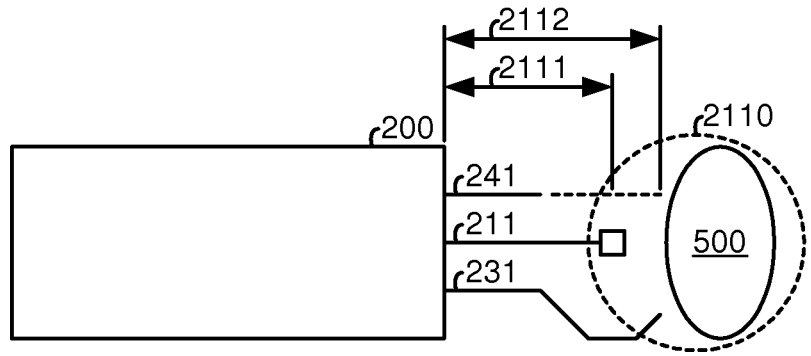

In FIG. 8b, the articulated tool instrument 241 is shown being inserted along its insertion axis (dotted line). A minimum insertion distance 2111 is specified which represents a minimum insertion point at which the working end of the instrument 241 is expected to enter the FOV 2110 of the camera 211. A maximum insertion distance 2112 is also specified which represents a maximum insertion point (with safety margin) beyond which the working end of the instrument 241 may strike the object 500. In the event that the instrument 241 reaches the maximum insertion distance 2112 without entering the FOV 2110 of the camera 211 for some reason, for safety purposes, further insertion of the instrument 241 by the assistant is prevented by locking the instrument in place.

Figure 8C:
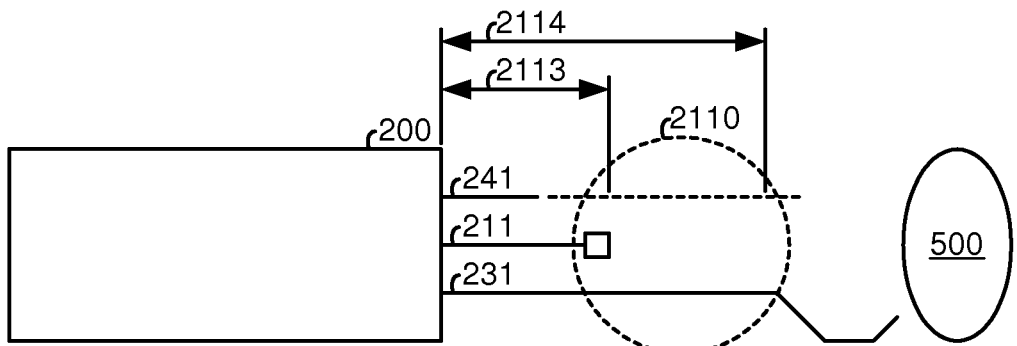

In FIG. 8c, the articulated tool instrument 241 is shown being inserted along its insertion axis (dotted line), but with the camera 211 (and possibly also the entry guide 200) moved back away from its original position by the operator. In this case, the operator can capture control of the instrument 241 sooner during the insertion. The minimum and maximum insertion distances, 2113 and 2114, are also adjusted as the field of view (FOV) 2110 of the camera 211 moves. In particular, the minimum insertion distance 2113 is adjusted so that it still represents the minimum insertion point at which the working end of the instrument 241 is expected to enter the camera's FOV 2110. The maximum insertion distance 2114, however, now represents an insertion distance that is near (or on the boundary) of where the FOV 2110 intersects the insertion plane of the instrument 241. Note that in this case, the maximum insertion distance 2114 is before the object 500 since the object 500 is well beyond the camera's FOV 2110. When the object 500 is within the camera's FOV 2110, then the maximum insertion distance would be based instead on the distance to the object 500 as described in reference to FIG. 8b.

When the instrument 241 is being inserted and the maximum insertion distance is reached before it enters the view on the stereo vision display 45, in addition to the instrument 241 being locked in place for safety purposes, a warning message is preferably provided on the stereo vision display 45 to inform the operator that the instrument 241 is outside the display area and locked in place. The assistant may also be warned by the lighting of an LED, for example, on the instrument's manipulator. Audio warnings may also be provided, alternatively or in addition to these visual warnings, so as to be heard by the operator and/or assistant. In addition to such warnings, a tool position and identification indicator may be displayed in a boundary area extending around the display area in the stereo vision display 45, so that the operator knows approximately how far away and in which direction the instrument 241 currently is. Details for such a tool position and identification indicator may be found, for example, in U.S. Publication No. 2008/0004603 A1 entitled "Tool Position and Identification Indicator Displayed in a Boundary Area of a Computer Display Screen," which is incorporated herein by reference. With such knowledge of the approximate position of the instrument 241, the operator may then move the camera instrument 211 towards the working end of the instrument 241 until the working end is within view on the stereo vision display 45, at which time, control of the instrument 241 is switched to the operator according to the method described in reference to FIG. 2.

Although the various aspects of the present invention have been described with respect to a preferred embodiment, it will be understood that the invention is entitled to full protection within the full scope of the appended claims.

What is claimed is:

1. A robotic system comprising:
a camera;
an instrument manipulator;
an instrument that is mechanically coupled to the instrument manipulator;
an input device; and
a processor that is programmed to operatively couple the instrument manipulator to the input device upon determining that the instrument has entered an area of a field of view of the camera.

2. The robotic system of claim 1,
wherein the instrument manipulator is adapted to be manually movable and telerobotically actuated,
wherein the processor is programmed to receive an indication that a first operator is to have manual control of the instrument manipulator and allow such manual control in response to the indication, and
wherein the processor is programmed to operatively couple the instrument manipulator to the input device by switching control of the instrument manipulator from manual control by the first operator to telerobotic control by a second operator interacting with the input device upon determining that the instrument has entered the area of the field of view of the camera.

3. The robotic system of claim 2, further comprising:
means for providing the indication that the first operator is to have manual control of the instrument manipulator.

4. The robotic system of claim 1, further comprising:
means for providing a sensory indication when the processor has operatively coupled the instrument manipulator to the input device.

5. The robotic system of claim 1, wherein the processor is programmed to switch control of the instrument manipulator from a program control mode, in which the processor responds to programmed instructions stored in a memory, to an operator control mode, in which the processor responds to operator manipulation of the input device, by operatively coupling the instrument manipulator to the input device upon determining that the instrument has entered the area of the field of view of the camera.

6. The robotic system of claim 1, further comprising:
a display viewable by an operator interacting with the input device, wherein the area of the field of view of the camera corresponds to a view being displayed on the display.

7. The robotic system of claim 6, wherein the camera is a stereo camera, the display is a three-dimensional display, the field of view of the stereo camera is a three-dimensional volume, and the area of the field of view is a subspace of the three-dimensional volume.

8. The robotic system of claim 1, wherein the processor is programmed to determine that the distal end of the instrument has entered the area of the field of view of the camera by determining a pose of the instrument and a pose of the camera in a world reference frame, translating the pose of the instrument to a reference frame of the camera to create a pose of the instrument in the reference frame of the camera, and using the pose of the instrument in the reference frame of the camera to determine whether a distal end of the instrument is within the area of the field of view of the camera.

9. The robotic system of claim 8, further comprising:
a plurality of sensors including a first plurality of sensors coupled to a first plurality of joints of the instrument manipulator to sense states of the first plurality of joints;
wherein the processor is programmed to determine the pose of the instrument in the world reference frame by receiving information from the plurality of sensors and applying the information to one or more forward kinematics equations to generate a kinematically derived estimate for the pose of the instrument in the world reference frame.

10. The robotic system of claim 9,
wherein the instrument comprises a wrist joint, and wherein the plurality of sensors includes a sensor coupled to the wrist joint to sense a state of the wrist joint.

11. The robotic system of claim 9,
wherein the instrument is an articulated tool instrument having a plurality of instrument joints, and wherein the plurality of sensors includes a second plurality of sensors coupled to the plurality of instrument joints to sense states of the plurality of instrument joints.

12. The robotic system of claim 11, further comprising:
an entry guide;
wherein the camera is an articulated camera instrument; and
wherein distal ends of the articulated tool instrument and the articulated camera instrument are extendable out of a distal end of the entry guide.

13. The robotic system of claim 9, further comprising:
a second plurality of joints which cause movement of an image capturing end of the camera; and
a second plurality of sensors coupled to the second plurality of joints to sense states of the second plurality of joints;
wherein the processor is configured to determine the pose of the camera in the world reference frame by receiving joint state information from the second plurality of sensors and applying the joint state information to one or more forward kinematics equations.

14. The robotic system of claim 1, wherein the processor is programmed to determine that the instrument has entered the area of the field of view of the camera by identifying a distal end of the instrument in an area of an image captured by the camera, and wherein the area of the image corresponds to the area of the field of view of the camera.

15. The robotic system of claim 1, wherein the processor is programmed to command the slave manipulator so as to prevent further insertion of the instrument if the instrument has reached a maximum insertion distance.

16. The robotic system of claim 15, wherein the processor is programmed to issue a warning to an operator of the input device if insertion of the instrument has reached the maximum insertion distance without entering the area of the field of view of the camera.

17. A method implemented in a robotic system to operatively couple an instrument manipulator to an input device, the method comprising:
using a processor to operatively couple the instrument manipulator to the input device upon determining that an instrument, which is mechanically coupled to the instrument manipulator, has entered an area of a field of view of a camera.

18. The method of claim 17, further comprising:
receiving an indication at the processor that a first operator is to have manual control of movement of the instrument and allowing, by the processor, such manual control in response to the indication;
wherein the input device is operated by a second operator, and wherein using the processor to operatively couple the instrument manipulator to the input device comprises switching control of the instrument from the manual control by the first operator to telerobotic control by the second operator operating the input device upon determining that the instrument has entered the area of the field of view of the camera.

19. The method of claim 17, wherein using the processor to operatively couple the instrument manipulator to the input device comprises switching control of the instrument manipulator from a program control mode, in which the processor responds to programmed instructions stored in a memory, to an operator control mode, in which the processor responds to operator manipulation of the input device, upon determining that the instrument has entered the area of the field of view of the camera.

20. The method of claim 17, wherein the area of the field of view of the camera corresponds to a view being displayed on a display viewable by an operator interacting with the input device.

21. The method of claim 20, wherein the camera is a stereo camera, the display is a three-dimensional display, the field of view of the stereo camera is a three-dimensional volume, and the area of the field of view is a subspace of the three-dimensional volume.

22. The method of claim 17, further comprising:
using the processor to determine that the instrument has entered the area of the field of view of the camera by using the processor to determine a pose of the instrument and a pose of the camera in a world reference frame, using the processor to translate the pose of the instrument to a reference frame of the camera to create a pose of the instrument in the reference frame of the camera, and using the processor to use the pose of instrument in the reference frame of the camera to determine whether a distal end of the instrument is within the area of the field of view of the camera.

23. The method of claim 22, wherein using the processor to determine the pose of the instrument in the world reference frame comprises:
receiving information at the processor for joints which move the distal end of the instrument; and
using the processor to generate a kinematically derived estimate for the pose of the instrument in the world reference frame by applying the information for the joints to forward kinematics equations.

24. The method of claim 23, wherein the instrument comprises a wrist joint, and wherein the joints which move the distal end of the instrument include the wrist joint.

25. The method of claim 23, wherein the instrument is an articulated instrument having a plurality of instrument joints, wherein the instrument manipulator comprises at least one manipulator joint, and wherein the joints which move the distal end of the instrument include the plurality of instrument joints and the at least one manipulator joint.

26. The method of claim 23, wherein using the processor to determine the pose of the camera in the world reference frame comprises receiving information at the processor for joints which move an image capturing end of the camera and using the processor to apply the information for the joints to forward kinematics equations.

27. The method of claim 17, further comprising:
using the processor to determine that the instrument has entered the area of the field of view of the camera by identifying a distal end of the instrument in an area of an image captured by the camera, wherein the area of the image corresponds to the area of the field of view of the camera.

28. The method of claim 17, further comprising:
using the processor to command the instrument manipulator to prevent further insertion of the instrument if the instrument has reached a maximum insertion distance.

29. The method of claim 28, further comprising:
using the processor to issue a warning to an operator of the input device if the processor has determined that insertion of the instrument has reached the maximum insertion distance without entering the area of the field of view of the camera.

* * * * *